(12) United States Patent
Babkes et al.

(10) Patent No.: US 6,325,785 B1
(45) Date of Patent: Dec. 4, 2001

(54) SPUTUM TRAP MANIFOLD WITH NESTED CAPS

(75) Inventors: Mitch Babkes, Maryland Heights; Alan B. Ranford, Creve Coeur; Kurt E. Yaeger, O'Fallon, all of MO (US)

(73) Assignee: Sherwood Services AG, Schaffausen (CH)

( * ) Notice: Subject to any disclaimer, the term of this patent is extended or adjusted under 35 U.S.C. 154(b) by 0 days.

(21) Appl. No.: 09/128,280

(22) Filed: Aug. 3, 1998

Related U.S. Application Data

(60) Provisional application No. 60/055,702, filed on Aug. 14, 1997.

(51) Int. Cl.[7] .............................. A61M 1/00; B65D 21/00; B65D 85/62; B65D 43/03; A62B 9/04
(52) U.S. Cl. ...................... 604/319; 604/317; 206/514; 220/781; 128/202.27; 128/912
(58) Field of Search .................... 604/317, 315, 604/118–119, 319–23; 128/898, 200.24, 202.27, 909, 911, 912; 215/316; 220/718, 675, 694, 724, 780–81; 600/562, 573, 577; 206/514–520, 828

(56) References Cited

U.S. PATENT DOCUMENTS

| 3,987,930 | * 10/1976 | Fuson | ...................................... 220/352 |
| 5,098,410 | 3/1992 | Kerby et al. | ........................... 604/256 |
| 5,598,840 | 2/1997 | Iund et al. | ....................... 128/207.14 |
| 5,792,126 | * 8/1998 | Tribastone et al. | .................. 604/319 |

FOREIGN PATENT DOCUMENTS

| WO 84/01805 | 5/1984 | (WO) . |
| WO 96/34636 | 11/1996 | (WO) . |

* cited by examiner

Primary Examiner—Angela D. Sykes
Assistant Examiner—Patricia M. Bianco
(74) Attorney, Agent, or Firm—Mark S. Leonardo, Esq.; Peter B. Sorell, Esq.; Brown Rudnick Freed & Gesmer, PC (57) ABSTRACT

The present invention relates to a sputum trap for an aspiration and respiratory support system which includes a manifold attachable to a specimen collection vial that is interposed between, and attached to, a suction control device and suction catheter device. The sputum trap allows for the collection of sputum directly from a patient through a suction catheter without causing a loss of Positive End Expiratory Pressure (PEEP) in the respiratory support system. The manifold includes a manifold body that has a first connector and a second connector for attachment to the suction control device and suction catheter, respectively, and an open port for secure attachment to the specimen collection vial. The manifold body further includes tethered first and second caps adapted for sealing the first and second connectors respectively from fluid flow communication once sufficient sputum has been collected in the specimen collection vial. A nest is formed on the top portion of the manifold body for conveniently storing the first and second caps during the collection of sputum without interfering with the operation of device.

24 Claims, 7 Drawing Sheets

SPUTUM TRAP MANIFOLD WITH NESTED CAPS

CROSS-RELATED APPLICATIONS

This patent application claims priority from United States Provisional Application Serial No. 60/055,702, filed on Aug. 14, 1997, by Babkes et al., the entire contents of which are hereby incorporated herein by reference.

BACKGROUND OF THE INVENTION

1. Field of the Invention

This invention relates generally to an apparatus used in the collection of sputum directly from a patient in a respiratory support system and more particularly to a sputum trap manifold that provides a convenient storage site for storing caps used to seal the connectors of the manifold. More specifically, the present invention relates to a sputum trap manifold that forms a nest adapted to conveniently store the caps prior to detachment of the sputum trap manifold from the respiratory support system.

2. Prior Art

Respiratory support systems used for the ventilation of critically ill patients are now commonly used in medical facilities. Typically, a prior art respiratory support system includes a tracheal tube positioned either directly, or through the nose or mouth, into the trachea of a patient, a manifold connected to the tracheal tube at one port positioned thereof, and a source of breathable gas connected at a second port thereof. The purpose of the respiratory support system is to assist the patient in maintaining adequate blood oxygenation levels without overtaxing the patients's heart and lungs.

While a patient is attached to the respiratory support system, it is periodically necessary to aspirate fluid from the patient's trachea or lungs. In the past, in order to accomplish aspiration, it has been necessary to disassemble part of the respiratory support system, either by removing the ventilator manifold therefrom or by opening a port of the manifold and inserting a small diameter suction tube down the tracheal tube and into the patient's trachea and lungs. However, there has been no solutions to the problem of sputum sample collection during aspiration, which also avoids the problem of respiratory support interruption.

U.S. Pat. No. 4,433,195 to Kee is generally exemplary of the prior art sputum sample collection during the aspiration of a patient's trachea and lungs without loss of respiratory support to the patient. The Kee device relates to an in-line sputum trap for a respiratory support system having a collection vial for receiving and storing a sputum specimen and a manifold that connects the sputum trap in fluid flow communication to a suction catheter used to aspirate a patient's trachea and lungs and a suction control valve which controls the flow of vacuum to the suction catheter. The sputum trap is designed for quick connect and disconnect with the suction catheter device and the suction control valve after having been used to collect a sputum sample from a patient. After collection of a sputum sample, the sputum trap is disconnected from the respiratory support system and the manifold is detached from the collection vial so that the collection vial can be sealed with a suitable cap for transportation. Unfortunately, a clinician removing the manifold from the collection vial may be inadvertently exposed to contaminates until the collection vial can be safely resealed.

U.S. Pat. No. 5,363,860 to Nakao et al. is generally exemplary of a sputum trap device that includes a pair of tethered caps used for sealing the inlet and outlet of the sputum trap's manifold after disconnection from the respiratory support system, thereby removing the need to detach the manifold from the collection vial. However, the Nakao et al. device suffers from drawbacks. One drawback is that the sputum trap has no convenient storage site to store the tethered caps so that the caps do not interfere with the operation of the suction catheter during aspiration of a patient's trachea and lungs. Another drawback is that there is no sanitary means provided in the Nakeo et al. device for preventing inadvertent contamination of the tethered caps by a clinician's hands during the aspiration procedure since the caps are permitted to freely dangle until used to seal the manifold's connectors.

As of yet, nothing in the prior art has addressed the problem of developing a nest or storage site on the body of the sputum trap manifold for conveniently storing in a sanitary environment a pair of tethered caps used to seal the inlet and outlet connectors of the sputum trap manifold. Moreover nothing in the prior art has addressed the need for developing a nest or storage site for nesting a pair of tethered caps so that the tethered caps do not interfere with the collection of a sputum specimen during aspiration of a patient's trachea and lungs.

OBJECTS AND SUMMARY OF THE INVENTION

The principle object of the present invention is to provide a sputum trap manifold having a storage site for conveniently nesting end caps that are used to seal the connectors of the manifold after the collection of sputum from the patient.

Another object of the present invention is to provide sealing end caps that are specifically adapted for nesting one cap on top of the other in the storage site formed on the sputum trap manifold.

A further object of the present invention is to provide end caps that are adapted for nested storage as well as for sealing engagement to the connectors of the sputum trap manifold.

A further important object of the present invention is to provide an improved sputum trap manifold with sealing end caps which does not require the removal of the manifold in order to seal off the collection vial after use.

Another principle object of the present invention is to provide a safe and sanitary means of sealing off the sputum trap manifold after the collection of sputum from the patient.

Another further principle object of the present invention is to provide a method for nesting end caps on the body of the manifold.

Another important object of the present invention is to provide a method of capping the manifold connectors which minimizes the opportunity for contamination to the clinician by the manifold's connectors during the capping procedure.

These and other objects of the present invention are realized in the preferred embodiment of the present invention, described by way of example and not by way of limitation. The preferred embodiment provides for a sputum trap manifold having an integral nesting site for storing end caps used to seal the connectors of the manifold after the collection of sputum from the patient. The sputum trap manifold comprises a manifold body having two end connectors adapted for connection to a source of suction and a suction catheter, respectively, as well as an outlet for attachment to a collection vial. The manifold body serves to divert and trap sputum being suctioned from the lungs of a patient and into the collection vial attached to the manifold. A nest is formed at the top portion of the manifold body for nesting two tethered end caps during sputum collection. Once aspiration of a patient's lungs is completed, the manifold is detached from the respiratory support system and the end caps are removed from the nest and sealably attached to the manifold's end connectors, thereby preventing the user from having to remove the manifold in order to reseal the collection vial and lessen exposure to contaminants from the collected sputum.

Finally, the present invention further includes a method for storing the end caps in the nest formed on the manifold and sealing the end connectors of a sputum trap manifold with the end caps without having to remove the manifold body from the collection vial. The method of nesting and sealing the end connectors of the sputum trap manifold comprises the steps of nesting one end cap over the other end cap in the nesting site after manufacturing, detaching the manifold's end connectors from the source of suction and suction catheter after the aspiration procedure has been completed, and removing the end caps from the manifold's nesting site. Once the end caps are removed, each end cap is sealingly attached to a respective end connector, thereby preventing the exposure of contaminants from collected sputum through the end connectors.

DETAILED DESCRIPTION OF THE INVENTION

Figure 1:
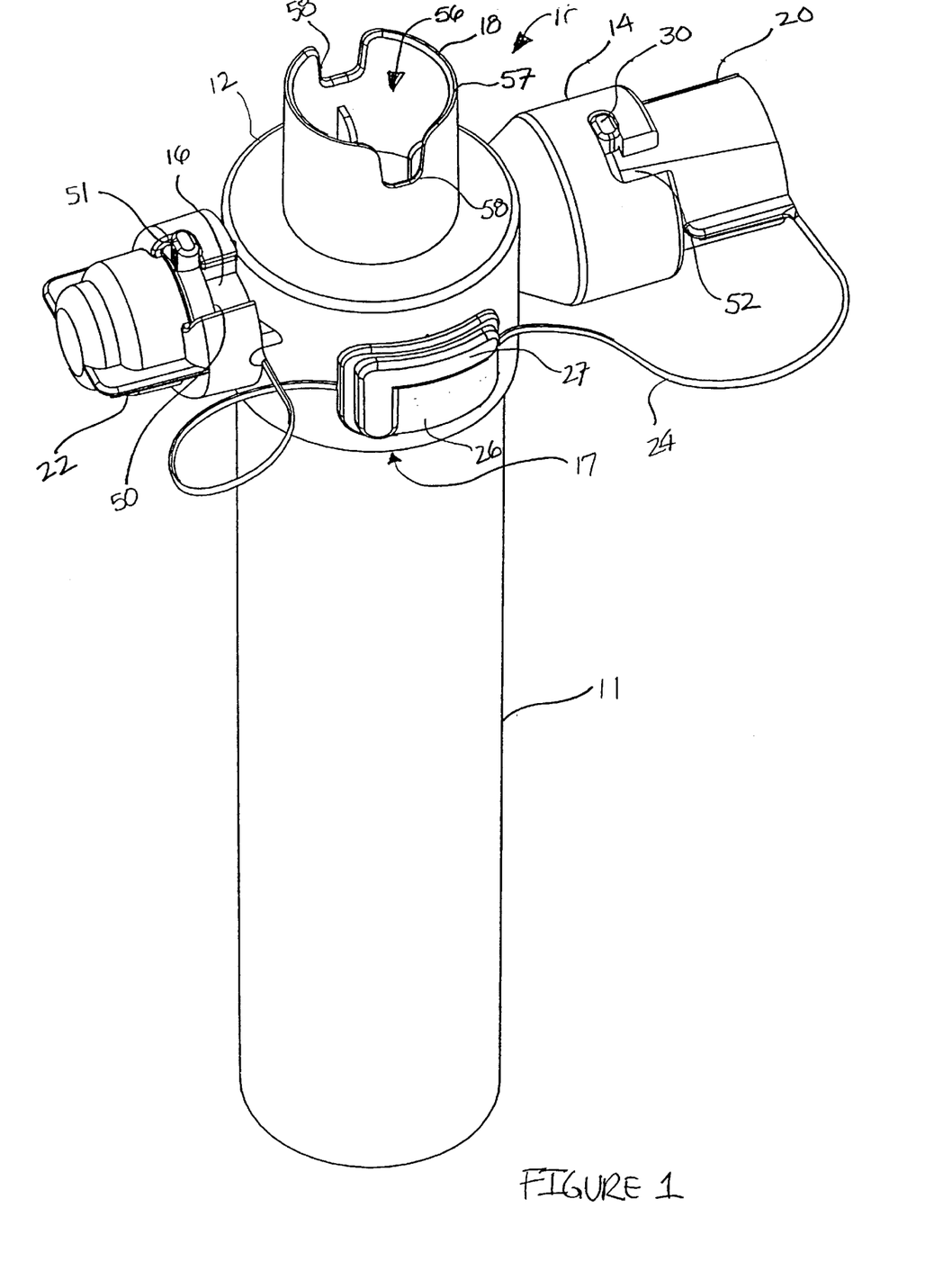
FIG. 1 is a perspective view of the sputum trap manifold showing the end caps in sealing engagement with the end connectors of the manifold body according to the present invention.

Referring to the drawings, the preferred embodiment of the sputum trap with nested end caps of the present invention is illustrated and generally indicated as 10 in FIG. 1. As shown in FIG. 1, the sputum trap 10 comprises a manifold body 12 that includes a female connector 14 that is opposed by a male connector 16 and an outlet 17 interposed therebetween that is adapted for attachment to a collection vial 11 for the collection of sputum from a patient. The manifold body 12 further includes a nest 18 formed on the top portion of the body 12 for storing a male end cap 22 on top of a female end cap 20 in a nested configuration therein. As illustrated in FIG. 1, the female and male connector end caps 20 and 22 are adapted to seal off female and male connectors 14 and 16, respectively, as well as to be stored inside the nest 18 prior to sealing off the connectors 14 and 16.

Figure 2:
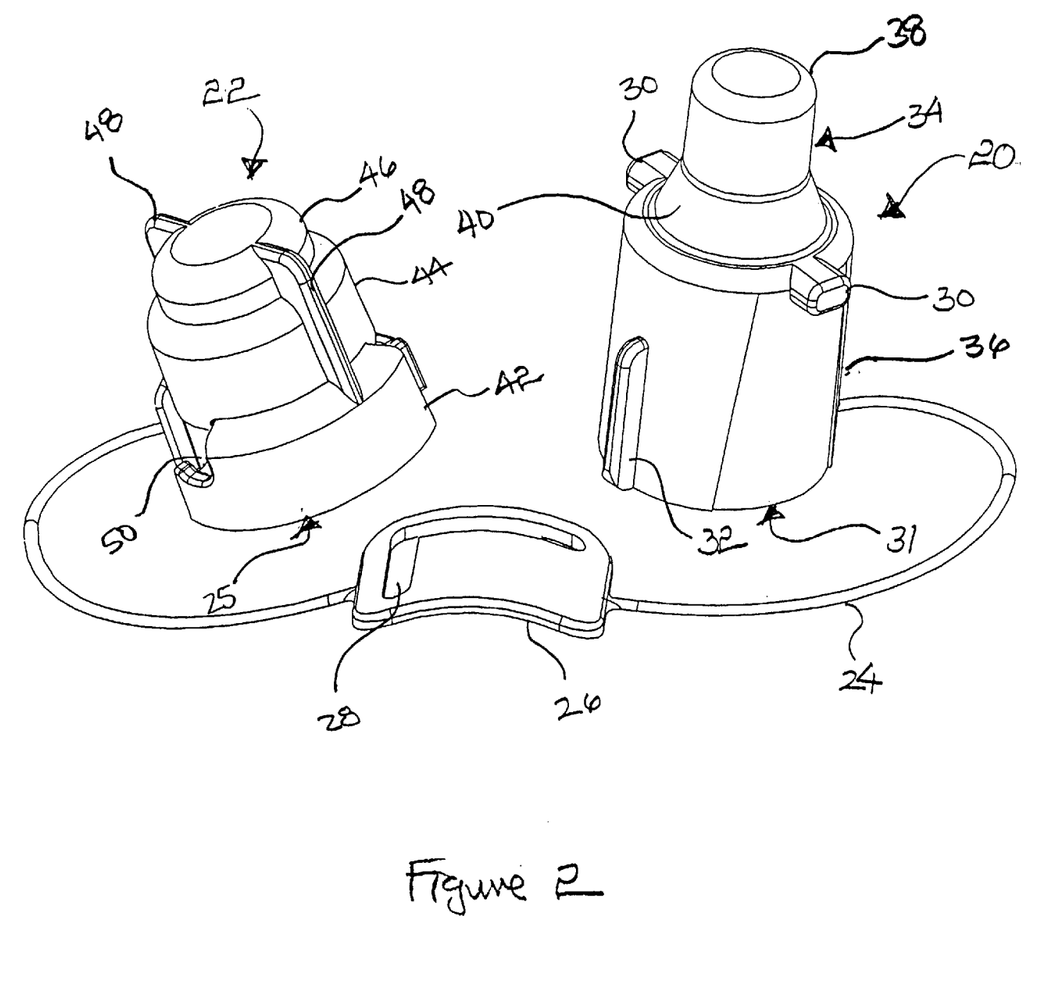
FIG. 2 is a perspective view of the tethered end caps according to the present invention.

FIG. 2 shows the female and male connector end caps 20 and 22 in greater detail. Both the female connector end cap 20 and the male connector end cap 22 are held together by a tether 24 at an attachment member 26 which is attachable to the manifold body 12 by an L-shaped attachment opening 28 formed through the body of the attachment member 26. Preferably, the attachment opening 28 is adapted for snap-fit connection to a similarly L-shaped attachment portion 27 formed on the manifold body 12, although the attachment member 26 may also be integrally formed with the manifold body 12.

Male connector end cap 22 comprises a cap body that forms a bottom portion 42, a mid portion 44 and a top portion 46 which are all in co-axial alignment with one another. Opposed L-shaped first bayonet slots 50 are formed on the bottom portion 42 of male connector end cap 22 and serve to securely engage the male connector end cap 22 to either the female connector end cap 20 during nesting or the male connector 16 when sealing the manifold body from fluid flow communication. Formed on the outside surface of the mid and top portions 44 and 46 of male connector end cap 22 are opposing grips 48 adapted for gripping between a user's thumb and forefinger when the user is either engaging the male connector end cap 22 to the female connector end cap 20 when nesting the two end caps 20 and 22 together or when sealing off the male connector 16 after the collection of sputum.

Female connector end cap 22 comprises a lower portion 36 and an upper portion 34. Upper portion 34 is a frusto-conical shaped body having a head section 38 and a conical section 40 that are adapted for engagement to either the nest 18 when nesting the two end caps 20 and 22 together or when sealing off the female connector 14 after the manifold body 12 is detached from the suction catheter and suction control valve (not shown). The lower portion 36 has an open interior cavity 31 having a tubular cross-section with opposed handles 32 formed on the surface thereof. Preferably, opposing handles 32 are bar-shaped and provide a convenient gripping surface for handling the female connector end cap 22 between the user's thumb and forefinger and, as shall be discussed in greater detail below, an integral component for nesting the female connector end cap 20 to the male connector end cap 22 in the nest 18 without contaminating the interior portion of either end cap 20 or 22 with the clinician's hands. Interposed between the upper portion 34 and the lower portion 36 are opposed securing members 30 which form radially extending protrusions adapted for securing the female connector end cap 20 to the nest 18 as well as assist in engaging and sealing off the female connector 14 of the manifold body 12. In securing the female connector end cap 20 to the female connector 14, the opposed securing members 30 engage opposed L-shaped second bayonet slots 52 by aligning and inserting each of the securing members 30 with a respective slot 52 until securely engaged thereto.

Figure 3:
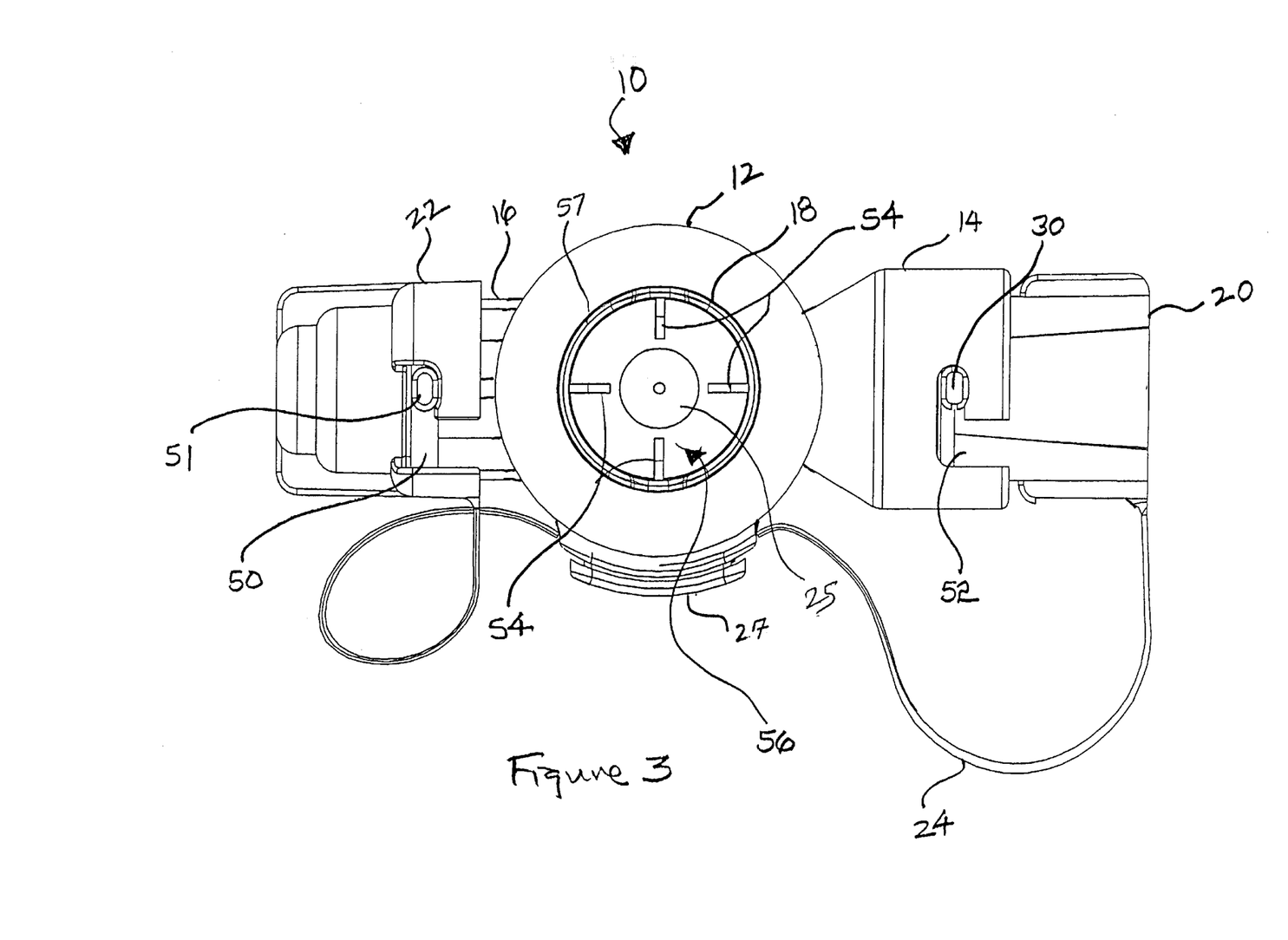
FIG. 3 is a top view of the sputum trap manifold showing the end caps in sealing engagement with the end connectors of the manifold body according to the present invention.

Referring to FIG. 3, a top view of nest 18 is illustrated. Nest 18 comprises a nest cavity 56 that forms a nest opening 57 at the top portion of cavity 56 and a plurality of opposed guide members 54 integrally formed along the interior wall at the bottom portion thereof. The bottom portion of nest cavity 56 also includes a bowl-shaped depression 25 that is adapted to receive the head section 38 of the female connector end cap 20 once the end cap 20 has been inserted and guided into position inside the nest 18. Preferably, the guide members 54 form equally spaced posts around the periphery of the nest cavity's 56 bottom portion in order to guide the upper portion 34 of the female connector end cap 20 into the nest cavity 56 as the end cap 22 is inserted into the nest 18. However, any number of guide members 56 positioned along the periphery of the nest cavity's 56 bottom portion in a manner suitable for guiding and receiving the female connector end cap's 20 upper portion 34 is felt to fall with the scope of the present invention. The nest opening 57 also includes opposed slots 58 formed on the lip thereto that are adapted to receive respective securing members 30 when inserting the female connector end cap 22 into the nest 18.

Figure 4:
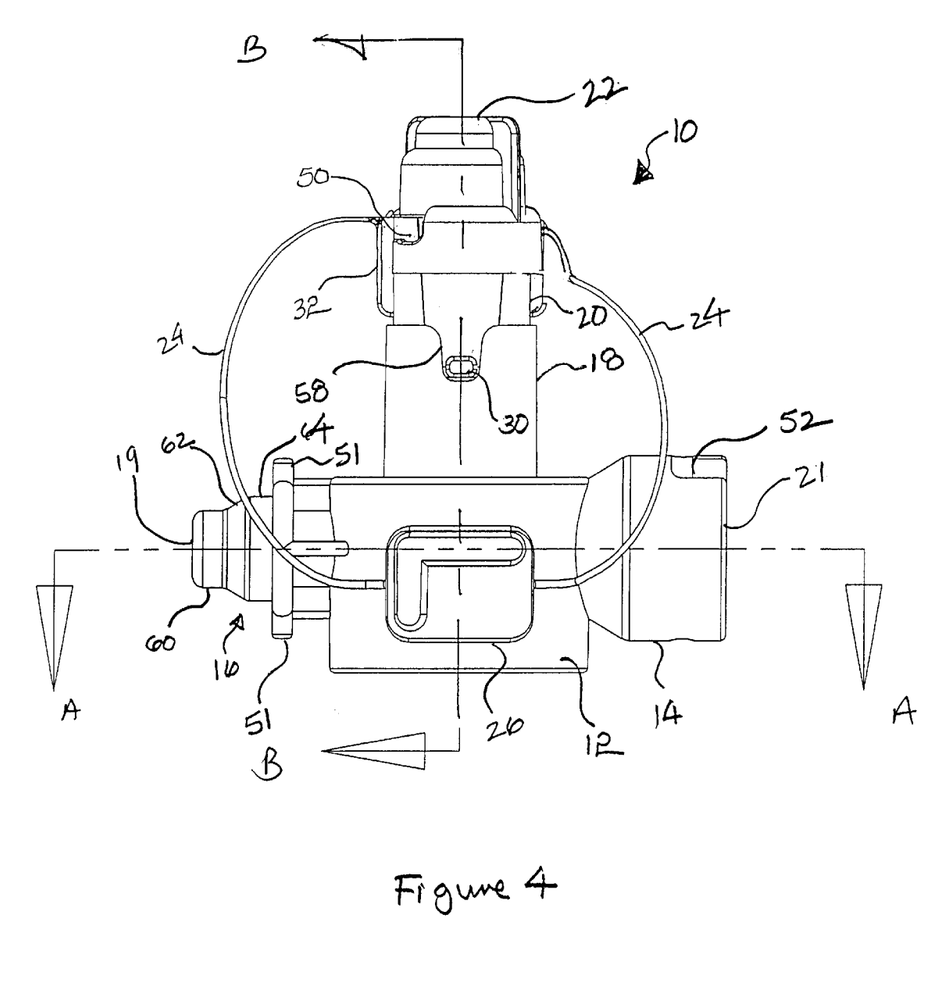
FIG. 4 is a side view of the sputum trap manifold showing the end caps nested in the manifold's nest according to the present invention.

Referring to FIG. 4, a more detailed description of the female and male connectors 14 and 16 will be discussed. Male connector 16 has a generally conical shape comprising a top section 60, a mid section 62 and a bottom section 64 with a first opening 19 that is in fluid flow communication with a manifold chamber 74 (see FIG. 5) of manifold body 12 and forms the free end of connector 16. In order to engage the first bayonet slots 50 of the male connector end cap 22 and seal the male connector 16 from fluid flow therethrough, opposed connecting members 51 that form protruding arms are provided on connector 16. These protruding arms of the connecting members 51 are adapted for insertion into the L-shaped slots 50 and rotated therein so as to establish a firm connection between the male connector 16 and the male connector end cap 22.

Female connector 14 has a frustoconical shape with a second opening 21 formed along the edge of connector 14 that is in fluid flow communication with the manifold chamber 74 and a neck 23 that is integrally formed to the manifold body 12. An opposed L-shaped second bayonet slots 52 are formed on the body of female connector 14 that extends from the connector's 14 free end. In order to engage the second bayonet slots 52 of female connector 14, the securing members 30 of the female connector end cap 20 are inserted into the L-shaped slots 52 and rotated therein so as to establish a firm connection between the connector 14 and the end cap 20.

Figure 5:
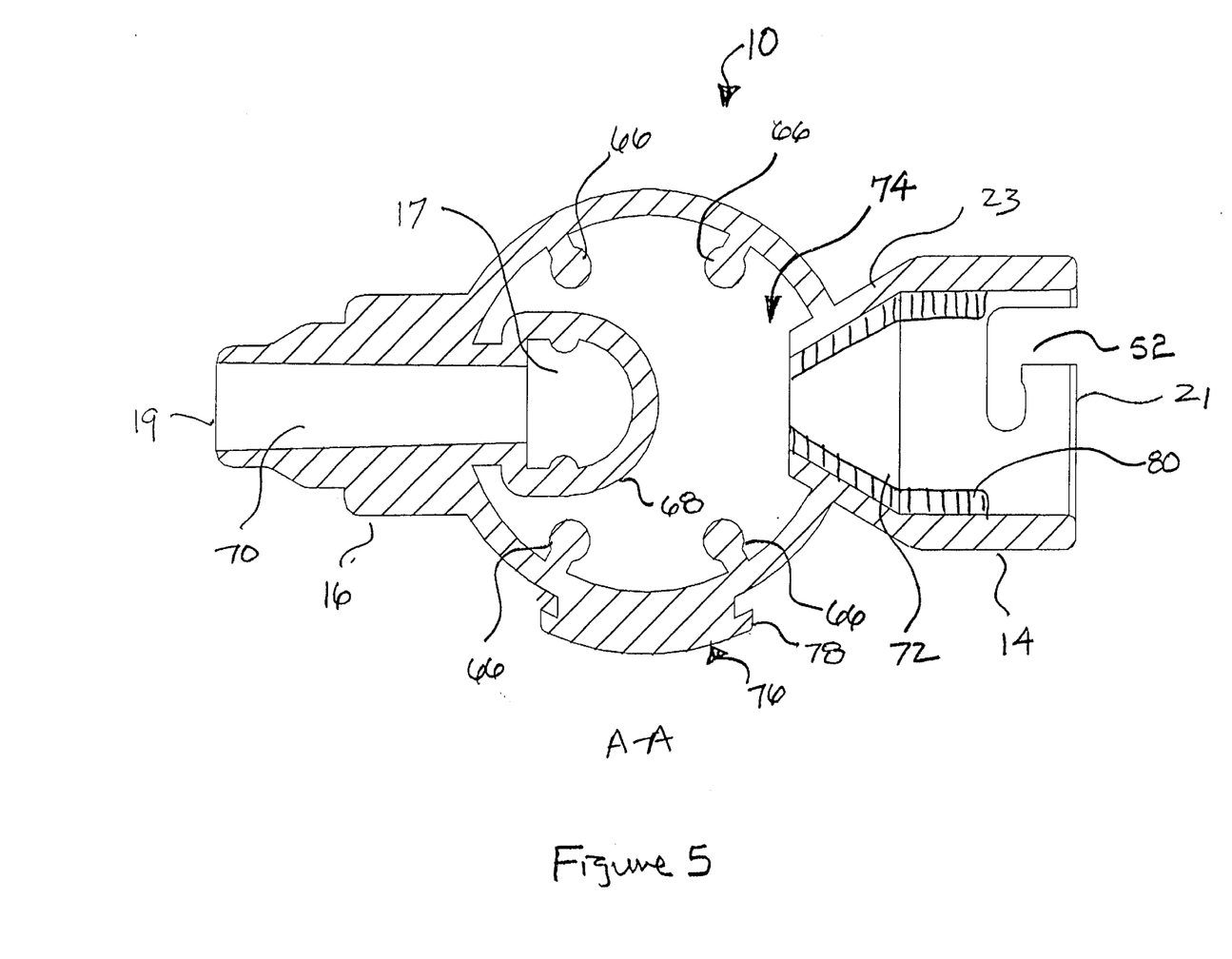
FIG. 5 is a cross section view of the manifold body along lines A—A showing the end caps nested in the manifold's nest according to the present invention.

Referring to FIG. 5, the interior of the manifold body 12 will be discussed in greater detail. As noted above, the manifold body 12 comprises an manifold cavity 74 that is in fluid flow communication with the male connector's 16 first opening 19 and the manifold cavity 74 through a first channel 70 interposed therebetween. Fluid flow communication is also established between a second opening 21 of female connector 14 and the manifold cavity 74 through a second channel 72 interposed therebetween. A splash guard 68 is provided at one end of the manifold cavity 74 facing the entrance to the first channel 70 for diverting aspirated sputum from the patient downward through the outlet 17 and into the collection vial 11 attached thereto. Thus, a first fluid pathway is established through the first channel 70, a second fluid pathway is established through the second channel 72, and a third fluid pathway is established between the first and second channels 70 and 72 through the collection vial. A seal 80 may also be provided along a portion of the interior surface of the female connector 14 for establishing and maintaining a secure hermetic seal around the female connector end cap 20 when the end cap 20 is engaged thereto. Preferably, the seal 80 is made from a flexible plastic or rubber material, for example polyurethane, that is suitable for creating a hermetic seal. Finally, a plurality of strengthening members 66 are provided around the lower periphery of the manifold cavity 74 for reinforcing and strengthening the manifold body 12.

Figure 6:
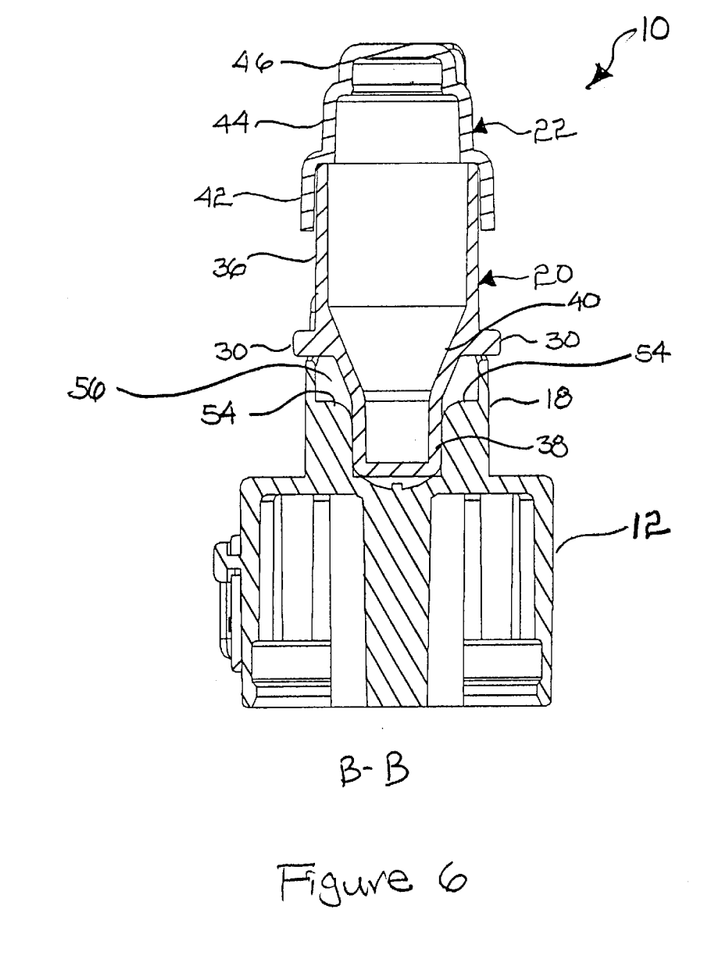
FIG. 6 is a cross-section view of the manifold body along lines B—B showing the end caps nested in the manifold's nest according to the present invention.
Figure 7:
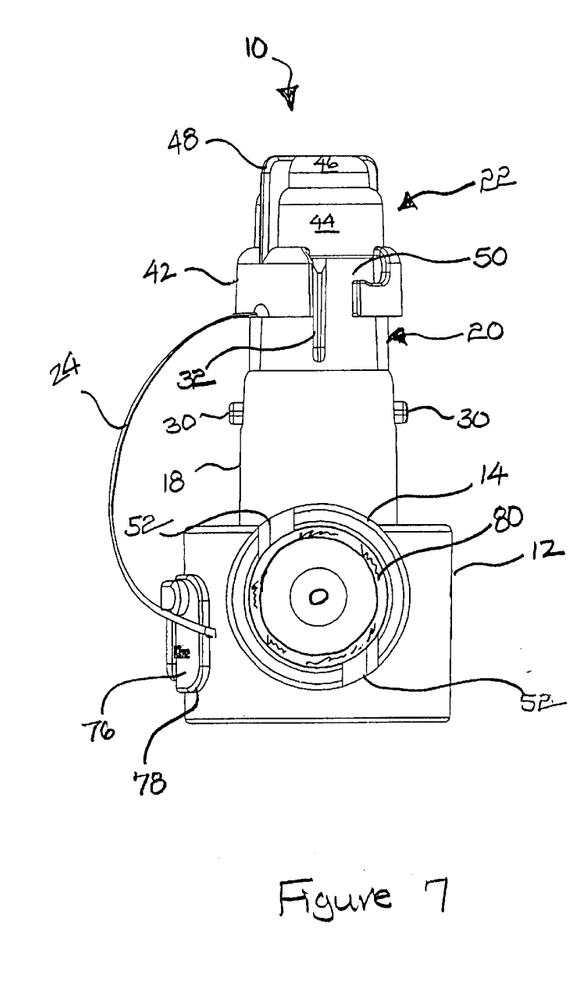
FIG. 7 is an end view of the manifold body according to the present invention.

Referring back to FIGS. 3 and 4, the method for nesting the female and male connector end caps 20 and 22 in the nest 18 will now be discussed in greater detail. After manufacturing and prior to engaging the sputum trap 10 to the suction catheter and suction control valve the female and male connector end caps 20 and 22 are stored in the nest 18 so that neither end caps 20 and 22 nor the tether 24 interfere with the operation of the closed system suction catheter. To nest female and male connector end caps 20 and 22, the head section 38 of female connector end cap 22 is first inserted into the nest 18 so that the opposed securing members 30 engage respective opposed slots 58. When the head section 38 enters the nest 18 it is guided by the guiding members 54 so that the section 38 comes in contact with the bowl-shaped depression 25 located at the bottom portion of nest 18. Once the female connector end cap 20 is fully inserted into the nest 18, the user grips the outer surface of the male connector end cap 22 and orients the cavity 25 of end cap 22 over the open bottom portion of the female connector end cap 20 already seated in the nest 18 as illustrated in FIG. 6. When placing the male connector end cap 22 over the female connector end cap 20 the user orients the first bayonet slots 50 of the male connector end cap 22 over the handles 32 of the female connector end cap 20 in such a manner that minimal rotation of the end cap 20 around the other end cap 22 is possible as shown in FIG. 7.

Once the patient has been sufficiently aspirated and sputum collected in the collection vial 11, the female and male connectors 14 and 16 of sputum trap 10 are disengaged from the suction catheter and suction control valve, respectively. After the sputum trap 10 is disengaged, the male connector end cap 22 is removed from its nested position on the female connector end cap 20 and attached in sealing engagement to the male connector 16 by aligning and engaging the first slots 50 of the end cap 22 with the connecting members 51 of the connector 16. Similarly, once the male connector end cap 22 is nested, the female connector end cap 20 is removed from the nest 18 and the upper portion 34 thereof inserted in sealing engagement with the female connector 14 in such a manner that the securing members 30 of the end cap 20 fully engage the L-shaped second bayonet slots 52 of female connector 14. In this sealed state the collection vial 11 and its attached sealed manifold can be safely stored and transported without fear of exposing a user to contaminants.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

We claim:

1. A manifold for attachment to a collection vial comprising:

a manifold body, said manifold body forming a first connector for attachment to a suction catheter, a second connector for attachment to a suction control device and an outlet for attachment to the collection vial, said manifold body including a first cap and a second cap, each of which include open end portions, for sealing said first and second connectors respectively, said manifold body further including a nest defining a cavity configured for receiving at least a portion of said first and second caps to facilitate storing said first and second caps in an open end relationship, wherein said open end of one of said first and second caps is configured for engagement with said open end of the other of said first and second caps for preventing contamination of said first and second end caps.

2. The manifold according to claim 1, wherein said first cap includes a top portion and a bottom portion, said bottom portion being adapted for storage inside said cavity of said nest.

3. The manifold according to claim 2, wherein said second cap includes an interior space, said interior space adapted for receiving said top portion of said first cap.

4. The manifold according to claim 1, wherein said first and second caps are tethered to said manifold body.

5. The manifold according to claim 1, wherein the nest includes at least one guide member having at least a portion thereof disposed within the cavity.

6. The manifold according to claim 1, wherein the nest includes a plurality of guide members being formed along an inner wall of the nest.

7. A manifold for attachment to a collection vial comprising:
a manifold body, said manifold body forming a first connector for attachment to a suction catheter, a second connector for attachment to a suction control device and an outlet for attachment to the collection vial, said manifold body including a first cap and a second cap, each of which include open end portions, for sealing said first and second connectors respectively, said manifold body further including a nest for storing said first and second caps in an open end relationship, wherein said open end of one of said first and second caps is coupled to said open end of the other of said first and second caps for preventing contamination of said first and second end caps, said cavity adapted for storing said first cap, wherein said nest further includes opposed slots.

8. The manifold according to claim 7 wherein said first cap includes opposed securing members, said securing members being adapted for engagement with said opposed slots.

9. A manifold for attachment to a collection vial comprising:
a manifold body, said manifold body forming a first connector for attachment to a suction catheter and a second connector for attachment to a suction control device, said manifold body including a first cap and a second cap for sealing said first and second connectors respectively, said manifold body further including a nest defining a cavity configured for receiving at least a portion of said first and second caps to facilitate storing said first and second caps, wherein said first and second caps are stacked one on top of another in an open end relationship, wherein an open end of one of said first and second caps is configured for engagement with and stacked on top of an open end of the other of said first and second caps for preventing contamination of said first and second end caps.

10. The manifold according to claim 9, wherein said first cap includes a top portion and a bottom portion, said bottom portion being adapted for storage inside said cavity of said nest.

11. The manifold according to claim 10, wherein said second cap includes an interior space, said interior space adapted for receiving said top portion of said first cap.

12. The manifold according to claim 9, wherein said first and second caps are tethered to said manifold body.

13. The manifold according to claim 9, wherein the nest includes at least one guide member having at least a portion thereof disposed within the cavity.

14. The manifold according to claim 9, wherein the nest includes a plurality of guide members being formed along an inner wall of the nest.

15. A manifold for attachment to a collection vial comprising:
a manifold body, said manifold body forming a first connector for attachment to a suction catheter and a second connector for attachment to a suction control device, said manifold body including a first cap and a second cap for sealing said first and second connectors respectively, said manifold body further including a nest for storing said first and second caps, wherein said first and second caps are stacked one on top of another, in an open end relationship, wherein an open end of one of said first and second cap is stacked on top of an open end of the other of said first and second end caps for preventing contamination of said first and second end caps, said cavity adapted for storing said first cap, wherein said nest further includes opposed slots.

16. The manifold according to claim 15, wherein said first cap includes opposed securing members, said securing members being adapted for engagement with said opposed slots.

17. A manifold for attachment to a collection vial comprising:
a manifold body, said manifold body forming a first connector for attachment to a suction catheter and a second connector for attachment to a suction control device, said manifold body including a first cap and a second cap for sealing said first and second connectors respectively, said manifold body fuirther including a nest defining a cavity configured for receiving at least a portion of said first and second caps to facilitate storing said first and second caps, wherein said first and second caps are stacked one on top of another, respectively, said first cap being stored in said nest and said second cap is stacked on top of said first cap in an open end relationship, wherein an open end of said second cap is configured for engagement with and stacked on top of an open end of said first cap for preventing contamination of said first and second end caps.

18. The manifold according to claim 17, wherein said second cap includes a space, said space adapted for receiving said top portion of said first cap.

19. The manifold according to claim 18, wherein said second cap includes an interior space, said interior space adapted for receiving said top portion of said first cap.

20. The manifold according to claim 17, wherein said first and second caps are tethered to said manifold body.

21. The manifold according to claim 17, wherein the nest includes at least one guide member having at least a portion thereof disposed within the cavity.

22. The manifold according to claim 17, wherein the nest includes a plurality of guide members being formed along an inner wall of the nest.

23. A manifold for attachment to a collection vial comprising:
a manifold body, said manifold body forming a first connector for attachment to a suction catheter and a second connector for attachment to a suction control device, said manifold body including a first cap and a second cap for sealing said first and second connectors respectively, said manifold body further including a nest for storing said first and second caps, wherein said first and second caps are stacked one on top of another, respectively, said first cap being stored in said nest and said second cap is stacked on top of said first cap in an open end relationship, wherein an open end of said second cap is stacked on top of an open end of said first cap for preventing contamination of said first and second end caps, said cavity adapted for storing said first cap, wherein said nest further includes opposed slots.

24. The manifold according to claim 23, wherein said first cap includes opposed securing members, said securing members being adapted for engagement with said opposed slots.

* * * * *